US 11,168,045 B2

(12) United States Patent
Moreo

(10) Patent No.: US 11,168,045 B2
(45) Date of Patent: Nov. 9, 2021

(54) PROCESS FOR METHANOL PRODUCTION

(71) Applicant: Casale SA, Lugano (CH)

(72) Inventor: Pietro Moreo, Lugano (CH)

(73) Assignee: Casale SA, Lugano (CH)

( * ) Notice: Subject to any disclaimer, the term of this patent is extended or adjusted under 35 U.S.C. 154(b) by 0 days.

(21) Appl. No.: 16/973,127

(22) PCT Filed: Apr. 10, 2019

(86) PCT No.: PCT/EP2019/059034
§ 371 (c)(1),
(2) Date: Dec. 8, 2020

(87) PCT Pub. No.: WO2019/233656
PCT Pub. Date: Dec. 12, 2019

(65) Prior Publication Data
US 2021/0253506 A1    Aug. 19, 2021

(30) Foreign Application Priority Data

Jun. 8, 2018 (EP) ..................................... 18176675

(51) Int. Cl.
*C07C 29/152*    (2006.01)
*C01B 3/50*    (2006.01)
(Continued)

(52) U.S. Cl.
CPC ............ *C07C 29/152* (2013.01); *B01J 8/008* (2013.01); *B01J 8/009* (2013.01); *B01J 8/0257* (2013.01); *C01B 3/503* (2013.01); *C01B 32/40* (2017.08); *C01C 1/0488* (2013.01); *C01B 2203/061* (2013.01); *C01B 2203/068* (2013.01)

(58) Field of Classification Search
CPC ..... C07C 29/152; C01C 1/0488; C01B 3/503; C01B 32/40; C01B 2203/061; C01B 2203/068; B01J 8/0257; B01J 8/008; B01J 8/009
See application file for complete search history.

(56) References Cited

U.S. PATENT DOCUMENTS

2011/0236293 A1   9/2011   Hardman et al.
2012/0148472 A1   6/2012   Ahmed et al.

FOREIGN PATENT DOCUMENTS

CN    1990442 A    7/2007
DE    3712008 A1    10/1988

OTHER PUBLICATIONS

Written Opinion of the International Searching Authority issued in connection with PCT/EP2019/059034.
(Continued)

*Primary Examiner* — Jafar F Parsa
(74) *Attorney, Agent, or Firm* — Akerman LLP

(57) ABSTRACT

Integrated process comprising: synthesis of methanol from a methanol synthesis gas (12); synthesis of ammonia from an ammonia make-up gas (25), and synthesis of carbon monoxide from a methane-containing stream, wherein: the synthesis of methanol provides a liquid stream of methanol (13) and a gaseous stream (14) of unreacted synthesis gas; a portion (14a) of said gaseous stream is separated as purge gas; said purge gas is subjected to a hydrogen recovery step, providing a hydrogen-containing stream (19) which is used as a hydrogen source for making the ammonia make-up gas, and a tail gas (20) which is used as a methane source for the synthesis of carbon monoxide by oxidation of a methane-containing stream.

17 Claims, 1 Drawing Sheet

(51) Int. Cl.
*C01C 1/04* (2006.01)
*C01B 32/40* (2017.01)
*B01J 8/00* (2006.01)
*B01J 8/02* (2006.01)

(56) References Cited

OTHER PUBLICATIONS

International Search Report issued in connection with PCT/EP2019/059034.

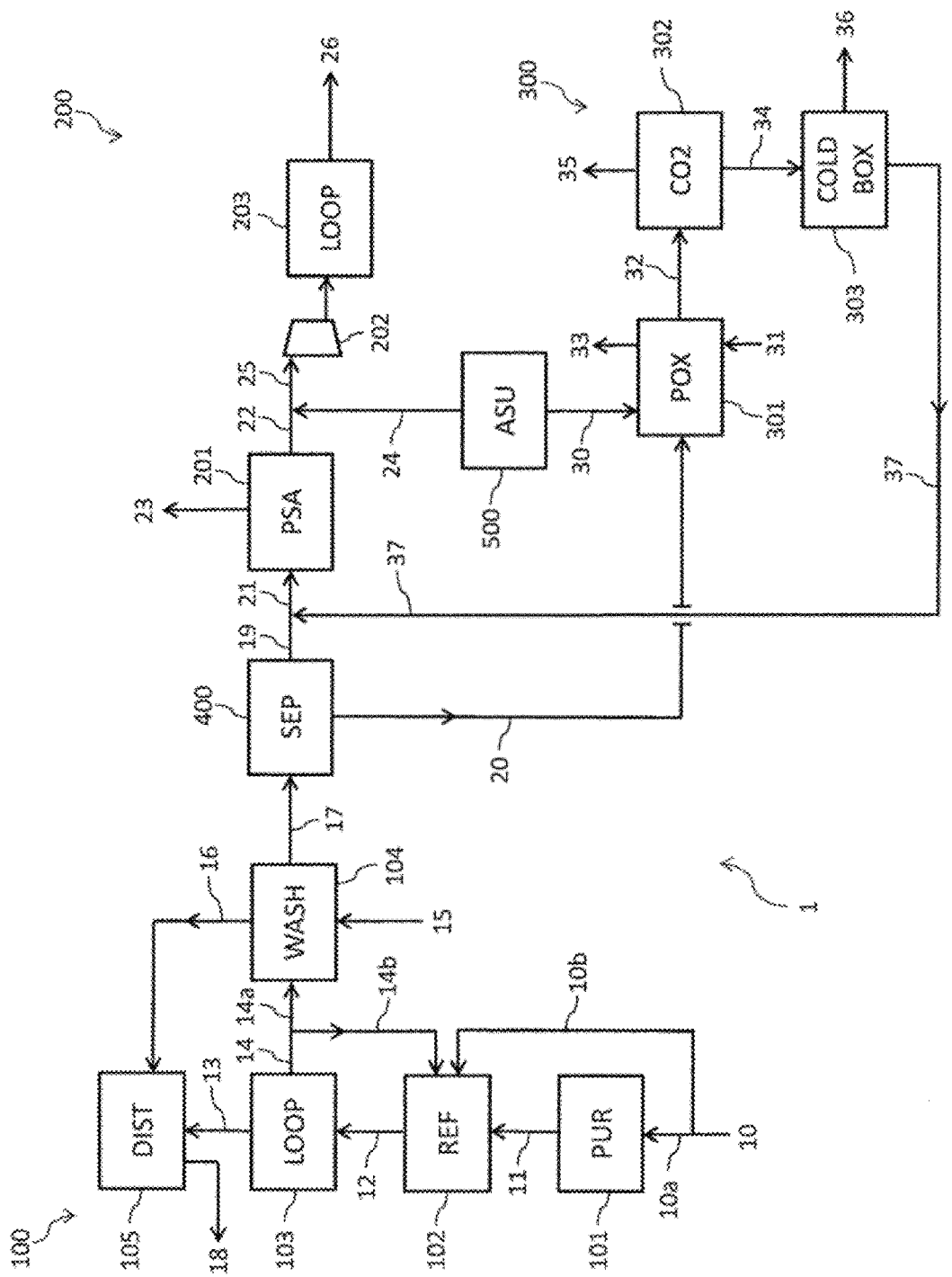

PROCESS FOR METHANOL PRODUCTION

CROSS-REFERENCE TO RELATED APPLICATIONS

This application is a national phase of PCT/EP2019/059034, filed Apr. 10, 2019, and claims priority to EP 18176675.9, filed Jun. 8, 2018, the entire contents of both of which are hereby incorporated by reference.

FIELD OF APPLICATION

The present invention relates to the field of methanol production.

PRIOR ART

A process for the synthesis of methanol basically comprises the production of a make-up synthesis gas containing carbon oxides (CO, $CO_2$) and hydrogen ($H_2$) by means of reforming or partial oxidation of a hydrocarbon feedstock in a front-end section, and the conversion of said make-up synthesis gas into methanol in a synthesis loop.

The conversion of the make-up gas into methanol is carried out at high temperature (200-300° C.) and high pressure (70-100 bar), in the presence of an appropriate catalyst, and involves the following reactions of hydrogenation of carbon oxides (CO, $CO_2$) and reversed water-gas shift:

$$CO + 2H_2 \leftrightarrows CH_3OH$$

$$CO_2 + 3H_2 \leftrightarrows CH_3OH + H_2O$$

$$CO_2 + H_2 \leftrightarrows CO + H_2O$$

Said reactions are characterized by unfavourable thermodynamic equilibrium conditions, and only a fraction of the make-up synthesis gas is converted into methanol per pass over the catalyst.

A stream containing unreacted gas is therefore separated from a stream of raw methanol obtained by the make-up gas conversion.

Said stream of raw methanol is typically refined in two stages: in a first stage light ends are removed, and in a second stage heavier ends and water are removed thus providing refined methanol of the desired quality.

The stream containing the unreacted gas is split into a first portion which is recirculated into the synthesis loop for further reaction and a second portion which is continuously withdrawn from the synthesis loop to avoid accumulation of inert compounds mainly including methane, argon and nitrogen. Said second portion is also referred to as purge gas stream and is mainly used as fuel in the burners of the reforming section.

However, the purge gas is withdrawn at a high pressure (about the same pressure of the synthesis loop), while the burners operate at low pressure. This means that the pressure energy of the purge gas is lost.

Furthermore, the purge gas contains reformed components, which are burnt to fuel the burners of the reforming section. This means that the energy used for the reforming is lost.

For the above reasons, the recycle of said purge gas as fuel in the burners is not fully satisfactory and efficient.

US 2011/0236293 discloses an integrated synthesis gas refinery plant and a process for simultaneous production of a hydrogen stream, a hydrogen rich synthesis gas, a hydrogen depleted synthesis gas and optionally a carbon monoxide stream.

SUMMARY OF THE INVENTION

The invention aims to overcome the drawbacks of the prior art. In particular, the invention aims to provide a more efficient recycle of the purge gas stream withdrawn from the synthesis loop of a methanol plant.

The idea forming the basis of the invention is to use the purge gas stream as feedstock for the synthesis of ammonia and carbon monoxide, while taking advantage of the synergies with the methanol production.

These aims are reached with an integrated process for the synthesis of methanol, ammonia and carbon monoxide according to claim 1.

Said process comprises:

a) a synthesis of methanol by catalytic conversion of a first synthesis gas, which is a gas containing hydrogen and carbon oxides;

b) a synthesis of ammonia by catalytic conversion of a second synthesis gas, which is an ammonia make-up gas including hydrogen and nitrogen, and c) a synthesis of carbon monoxide by oxidation of a methane-containing stream, wherein:

said step a) provides a liquid stream of methanol and a gaseous stream containing unreacted synthesis gas;

a portion of said gaseous stream containing unreacted synthesis gas is separated as a purge gas stream;

said purge gas stream is subjected to a hydrogen recovery step, obtaining a hydrogen-containing stream and a tail gas containing methane and CO, and at least part of said hydrogen-containing stream is a hydrogen source for the ammonia make-up gas subjected to conversion of step b), and at least part of said tail gas is a methane source for the methane-containing stream subjected to oxidation of step c).

Preferably, the first synthesis gas subjected to conversion of step a) is obtained by a step of conversion of a hydrocarbon feedstock. Said step of conversion may comprise partial oxidation of said hydrocarbon feedstock or, preferably, reforming of said hydrocarbon feedstock. The so obtained first synthesis gas is then advantageously compressed at a synthesis pressure of 70-100 bar. Said first synthesis gas is then converted into crude methanol at said synthesis pressure within a synthesis loop, and the so obtained crude methanol is separated into said liquid stream of methanol and said gaseous stream containing unreacted synthesis gas.

According to a preferred embodiment, said process comprises a step of air separation in a dedicated air separation unit (ASU), which provides a nitrogen stream and an oxygen stream. At least part of said nitrogen stream is a nitrogen source for said ammonia make-up gas and at least part of said oxygen stream acts as oxidant in the oxidation of said methane-containing stream. Part of said oxygen stream may also be used as a source of oxygen in the above step of conversion of the hydrocarbon feedstock into the first synthesis gas.

The gaseous stream containing unreacted synthesis gas advantageously splits into said purge gas stream and a stream which is recycled back to the step of conversion into crude methanol for further reaction.

According to a preferred embodiment, said hydrogen recovery step is performed by means of separating membranes.

Preferably, said purge gas stream is subjected, before undergoing said hydrogen recovery step, to a water washing step, wherein traces of methanol are absorbed in water and removed in an aqueous stream, thus providing a methanol-free purge gas stream. Said washing step is advantageous especially when separating membranes are used in the subsequent hydrogen recovery step, because methanol is removed which could be an issue for said membranes.

Preferably, the pressure of said hydrogen-containing stream, at the outlet of the separating membranes, is about 25-30 bar less than the pressure of the purge gas stream at the inlet of the separating membranes. Accordingly, the pressure decrease of said hydrogen-containing stream through the separating membranes is about 25-30 bar.

Preferably, the pressure of the tail gas, at the outlet of the separating membranes, is 2-4 bar less than the pressure of the purge gas stream at the inlet of the separating membranes. Accordingly, the pressure decrease of said tail gas through the separating membranes is about 2-4 bar.

Preferably, at least 90% of the hydrogen contained in the purge gas stream obtained by splitting the gaseous stream containing unreacted synthesis gas is recovered in the hydrogen recovery step and collected in said hydrogen-containing stream. Preferably, said hydrogen-containing stream has a hydrogen content of at least 85% (vol).

Preferably, at least 70% of the methane contained in said purge gas stream and at least 60% of the carbon monoxide contained therein are collected in the tail gas withdrawn from the hydrogen recovery step. Said tail gas preferably has a methane content of about 60% (vol) and a carbon monoxide content of about 2% (vol).

According to an embodiment of the invention, the synthesis of ammonia includes: a step of purification of said hydrogen-containing stream, providing a purified hydrogen-containing stream; mixing said purified stream with a suitable amount of nitrogen, providing said ammonia make-up gas, and compression of said make-up gas to a synthesis pressure in a multi-stage compressor. Said nitrogen is advantageously provided by the above mentioned ASU and is injected in said purified hydrogen stream at the suction of said multi-stage compressor.

Preferably, said step of purification is carried out in a pressure swing adsorption (PSA) unit. Advantageously, the pressure decrease through said PSA unit is of about 1 bar and the purified hydrogen-containing stream, at the outlet of said PSA unit, has a pressure in the range 40-50 bar.

The PSA unit advantageously recovers in said purified stream about 80-90% of the hydrogen initially present in the stream before purification. Said purified stream contains inert gases (i.e. methane and argon) in an amount preferably not greater than 2000 ppmv, more preferably in the range between 700 and 2000 ppmv. Said purified stream contains less than 10 ppm of compounds like CO, CO2, O2 and water, which represent poisons of the catalyst for the synthesis of ammonia.

A tail gas containing methane, hydrogen, nitrogen, CO, CO2, Ar and water is also withdrawn from said PSA unit. Preferably, said tail gas is at least partially recycled as a fuel to the step of conversion of the hydrocarbon feedstock into the first synthesis gas, for example to the burners of the reforming section.

According to an embodiment of the invention, the synthesis of carbon monoxide includes: subjecting the tail gas from the hydrogen recovery step and containing methane and carbon monoxide to partial oxidation (PDX) in a suitable PDX unit, wherein methane is oxidized into CO thus providing a CO-containing synthesis gas; subjecting said synthesis gas to a step of CO2 removal and then to a step of CO separation, obtaining a CO stream and a further hydrogen-containing stream.

Considering that the pressure drop of the PDX unit is of 8-10 bar, the operating pressure of said PDX unit is properly chosen so as to optimize the operation of the downstream CO separation unit. The CO separation unit may be a cold box or may contain separating membranes, depending on the requested final specification of the CO product.

Preferably, said further hydrogen-containing stream mixes with the hydrogen-containing stream obtained from the above mentioned hydrogen recovery step. In another embodiment, said further hydrogen-containing stream is recycled as fuel to the step of conversion of the hydrocarbon feedstock into the first synthesis gas, for example to the burners of the reforming section.

Another object of the present invention is a plant according to the attached claims.

Particularly, the plant is characterized by comprising:

means arranged to direct at least a portion of a hydrogen-containing stream from a methanol section to an ammonia section to provide at least part of the hydrogen required to obtain said ammonia make-up gas, and means arranged to direct at least a portion of a tail gas from the methanol section to a carbon monoxide section to provide at least part of the methane to oxidize.

The plant may further comprise:

an air separation unit providing a nitrogen stream and an oxygen stream, means arranged to direct at least a portion of said nitrogen stream to the ammonia section to provide at least part of the nitrogen required to obtain said ammonia make-up gas, and means arranged to direct at least a portion of said oxygen stream (30) to the carbon monoxide section to provide at least part of the oxidant for oxidation of methane.

The above means may include piping and the necessary items to properly direct the concerned gaseous stream, e.g. valves and a compressor or blower if appropriate.

The present invention has the following advantages.

A first advantage is the maximum exploitation of the energy content associated to the purge gas stream leaving the methanol synthesis loop as high pressure stream and containing valuable reformed components (i.e. hydrogen and carbon oxides), thus entailing a decrease of the overall energy consumption for manufacturing methanol, ammonia and carbon monoxide.

Another advantage is that the power of the synthesis gas compressor of the ammonia section is reduced compared to the prior art.

Moreover, the hydrocarbon purification sections typically present in the ammonia and carbon monoxide plants of the prior art are avoided. Furthermore, the section for the conversion of the hydrocarbon feedstock into synthesis gas and the shift reactor typically present in an ammonia plant of the prior art are also avoided.

In addition, the syngas generation section for CO production is reduced in size (about 5%) thanks to the CO present in the purge gas. Furthermore, the operation of the CO separation unit (Cold Box or membranes) is optimized thanks to the selection of the most suitable operating pressure for it and the upstream units.

Another advantage is that the boiler feed water (BFW) and the steam system are common for the three production facilities.

The present invention also has several advantages from a commercial point of view, in particular: reduced investment cost for coproduction compared to the three production lines for each product; attractive synergies in the investment for ASU which can be used as source of oxygen for methanol production and CO production and, at the same, it can be used as source of nitrogen for ammonia production.

The advantages of the invention will emerge even more clearly with the aid of the detailed description below relating to a preferred embodiment, as shown in FIG. 1.

DETAILED DESCRIPTION

The integrated plant 1 shown in FIG. 1 comprises a section 100 for the synthesis of methanol, a section 200 for the synthesis of ammonia and a section 300 for the synthesis of carbon monoxide. Said plant also comprises a membrane-based hydrogen recovery unit (HRU) 400 and an air separation unit (ASU) 500.

The methanol section 100 essentially includes a natural gas purification unit 101, a reforming unit 102, a synthesis loop 103, a water washing column 104 and a distillation unit 105. According to this example, the reforming unit 102 performs pure steam reforming in the presence of steam. The synthesis loop 103 essentially contains a catalytic reactor, a condensation section and a separator.

The reforming unit 102 produces a synthesis gas 12 which is compressed in a multi-stage compressor (not shown) and subsequently reacted in the synthesis loop 103. The synthesis loop 103 provides a liquid stream of methanol 13 and a gaseous stream of unreacted synthesis gas 14. The liquid stream of methanol 13 is sent to the distillation unit 105 and the gaseous stream of unreacted gas 14 is subjected to water washing in the column 104.

The gaseous stream 17 drawn off from the water washing column 104 feeds the hydrogen recovery unit 400 from which a hydrogen-containing stream 19 and a methane- and CO-containing tail gas 20 are released.

The ammonia section 200 receives said hydrogen-containing stream 19 and essentially includes a purification unit 201, a multi-stage gas compressor 202 and an ammonia synthesis loop 203. According to the example of the FIGURE, said purification unit 201 is a pressure swing adsorption (PSA) unit.

The carbon monoxide section 300 receives said methane- and CO-containing tail gas 20 and essentially includes a partial oxidation (PDX) unit 301, a CO2 removal section 302 and a CO separation unit 303. According to the example of the FIGURE, the CO separation unit 303 is a cold box.

More in detail, the operation of the plant 1 is the following.

A stream 10 of natural gas splits into a first portion 10a and a second portion 10b.

Said first portion 10a is supplied to the purification unit 101 of the methanol section 100, wherein sulfur and other contaminants are removed, thus providing a purified natural gas feedstock 11.

Said second portion 10b and said purified feedstock 11 are fed to the reforming unit 102, wherein they are reformed providing a synthesis gas 12. Said synthesis gas 12 contains carbon oxides (CO, $CO_2$), hydrogen and inert gases.

The synthesis gas 12 is compressed to a synthesis pressure of about 70-100 bar in a multi-stage compressor (not shown). The so-obtained compressed gas is supplied to the synthesis loop 103, wherein crude methanol is obtained and split into the above mentioned liquid stream of methanol 13 and gaseous stream of unreacted synthesis gas 14.

Said liquid stream of methanol 13 is subjected to purification into the distillation unit 105.

Said gaseous stream of unreacted synthesis gas 14 splits into a first portion 14a and a second portion 14b. Said first portion 14a (also referred to as purge gas stream) enters the washing column 104 which is also supplied with washing water 15 and wherein traces of methanol are removed in an aqueous stream 16, thus providing a methanol-free stream of unreacted synthesis gas 17. Said second portion 14b is, instead, recycled back to the reforming unit 102 for further reaction.

The methanol-free stream 17 feeds the hydrogen recovery unit 400, which separates the already mentioned hydrogen-containing stream 19 and tail-gas 20 containing inert components such as methane and carbon monoxide.

The hydrogen-containing stream 19 mixes with another hydrogen-containing stream 37 leaving the CO separation unit 303. The resulting hydrogen-containing stream 21 is supplied to the PSA unit 201 of the ammonia section 200, which provides a hydrogen purified stream 22 and a tail gas 23 containing methane, CO, CO2, H2, Ar, N2 and water. Said tail gas is, for example, used as fuel in the reforming unit 102 of the methanol section 100.

The pressure decrease through the PSA unit 201 is in the order of magnitude of 1 bar and the purified stream 22 is available at the suction of the syngas compressor 202 at a pressure of 40-50 bar.

Said purified stream 22 mixes, at the suction of the compressor 202, with nitrogen 24 provided by the ASU 500, forming an ammonia make-up synthesis gas 25.

The make-up gas 25 is compressed to the ammonia synthesis pressure in the compressor 202 and fed to the synthesis loop 203, which delivers ammonia 26 and a tail gas (not shown) which can be used to fuel the reforming unit.

The tail gas 20 from the HRU 400 is supplied to the PDX unit 301 of the carbon monoxide section 300, wherein the methane contained in said tail gas reacts with oxygen 30 and steam 31, thus providing a synthesis gas 32 with a high CO content, low CO2 content and low methane slip. The oxygen 30 is provided by the ASU 500.

Saturated high pressure steam (HPS) or medium pressure steam (MPS) is generated in the heat recovery system of the PDX unit 301 and is represented in the FIGURE by stream 33. Said steam is, for example, used as driving medium for the turbines of the ASU 500 after superheating in a section of the methanol plant.

The synthesis gas 32 enters the CO2 removal section 302, which provides a CO2-depleted synthesis gas 34 and a tail gas 35 mainly containing CO2. Said tail gas 35 is vented into the atmosphere.

The CO2-depleted synthesis gas 34 is sent to the cold box 303, which provides a CO-containing stream 36 and a hydrogen-containing tail gas 37. The stream 36 is exported from the plant. The stream 37 mixes with the hydrogen-containing stream 19 effluent of the HRU 400 to provide the inlet stream 21 of the PSA unit 201.

EXAMPLE

With a methanol section based on pure steam reforming and sized for 1500 MTD and with an ASU sized for 160 MTD of oxygen and 460 MTD of nitrogen, the process according to the invention allows to obtain about 550 MTD of ammonia and 150 MTD of CO.

What is claimed is:

1. An integrated process for the synthesis of methanol, ammonia and carbon monoxide, comprising:
   a) a synthesis of methanol by catalytic conversion of a first synthesis gas, which is a gas containing hydrogen and carbon oxides;
   b) a synthesis of ammonia by catalytic conversion of a second synthesis gas, which is an ammonia make-up gas including hydrogen and nitrogen, and
   c) a synthesis of carbon monoxide by oxidation of a methane-containing stream, wherein:
   said step a) providing a liquid stream of methanol and a gaseous stream containing unreacted synthesis gas;
   a portion of said gaseous stream containing unreacted synthesis gas is separated as a purge gas stream;
   said purge gas stream is subjected to a hydrogen recovery step, obtaining a hydrogen-containing stream and a tail gas containing methane and CO, and
   at least part of said hydrogen-containing stream is a hydrogen source for the ammonia make-up gas subjected to conversion of step b), and at least part of said tail gas is a methane source for the methane-containing stream subjected to oxidation of step c).

2. The process according to claim 1, comprising a step of air separation in a dedicated air separation unit, providing a nitrogen stream and an oxygen stream wherein at least part of said nitrogen stream is a nitrogen source for said ammonia make-up gas and at least part of said oxygen stream acts as oxidant in the oxidation of said methane- containing stream.

3. The process according to claim 1, wherein said purge gas stream is subjected to a water washing step before undergoing said hydrogen recovery step.

4. The process according to claim 1, wherein said hydrogen recovery step is performed by means of separating membranes.

5. The process according to claim 4, wherein the pressure of said hydrogen-containing stream, at the outlet of the separating membranes, is 25-30 bar less than the pressure of the purge gas stream at the inlet of the separating membranes.

6. The process according to claim 4, wherein the pressure of the tail gas, at the outlet of the separating membranes, is 2-4 bar less than the pressure of the purge gas stream at the inlet of the separating membranes.

7. The process according to claim 1, wherein at least 90% of the hydrogen contained in the purge gas stream is recovered in the hydrogen- containing stream.

8. The process according to claim 1, wherein at least 70% of the methane contained in the purge gas stream and at least 60% of the carbon monoxide contained therein are recovered in the tail gas.

9. The process according to claim 1, wherein the synthesis of ammonia includes the following steps:
   purification of said hydrogen-containing stream, providing a purified hydrogen-containing stream;
   mixing said purified stream with a suitable amount of nitrogen, providing the ammonia make-up gas;
   compression of said make-up gas to a synthesis pressure.

10. The process according to claim 9, wherein said purification is carried out in a pressure swing adsorption (PSA) unit, the pressure decrease through said PSA unit being of about 1 bar and the purified hydrogen-containing stream at the outlet of said PSA unit having a pressure in the range 40-50 bar.

11. The process according to claim 10, the synthesis of methanol including a step of conversion of a hydrocarbon feedstock into said first synthesis gas, wherein a tail gas containing methane, hydrogen, nitrogen, CO, CO2, Ar and water is withdrawn from said PSA unit and said tail gas is at least partially recycled as a fuel to said step of conversion.

12. The process according to claim 1, wherein the synthesis of carbon monoxide includes the following steps:
   subjecting the tail gas obtained from the hydrogen recovery step to partial oxidation, thus providing a CO-containing synthesis gas;
   subjecting said synthesis gas to a step of CO2 removal and then to CO separation, providing a CO stream and a further hydrogen-containing stream.

13. The process according to claim 12, wherein said further hydrogen-containing stream joins with the hydrogen-containing stream obtained from the hydrogen recovery step.

14. A plant comprising a section for the synthesis of methanol, a section for the synthesis of ammonia and a section for the synthesis of carbon monoxide, wherein the section for the synthesis of methanol comprises:
   a reforming section, wherein a hydrocarbon feedstock is reformed to provide a synthesis gas;
   a syngas compressor, which elevates the pressure of the synthesis gas to a synthesis pressure;
   a synthesis loop, providing a liquid stream of methanol and a gaseous stream containing unreacted synthesis gas;
   a hydrogen recovery unit, which receives a portion of said gaseous stream and provides a hydrogen-containing stream and a tail gas containing methane and CO,
   wherein the section for the synthesis of ammonia comprises a synthesis loop
   wherein an ammonia make-up gas including hydrogen and nitrogen is converted into ammonia,
   wherein the section for the synthesis of carbon monoxide comprises a partial oxidation reactor wherein methane is oxidized into carbon monoxide,
   said plant comprising:
   means arranged to direct at least a portion of said hydrogen-containing stream from the methanol section to the ammonia section to provide at least part of the hydrogen required to obtain said ammonia make-up gas, and
   means arranged to direct at least a portion of said tail gas from the methanol section to the carbon monoxide section to provide at least part of the methane to oxidize.

15. The plant according to claim 14, further comprising an air separation unit providing a nitrogen stream and an oxygen stream, and further comprising:
   means arranged to direct at least a portion of said nitrogen stream to the ammonia section to provide at least part of the nitrogen required to obtain said ammonia make-up gas, and means arranged to direct at least a portion of said oxygen stream to the carbon monoxide section to provide at least part of the oxidant for oxidation of methane.

16. The process according to claim 7, wherein said hydrogen-containing stream has a hydrogen content of at least 85% (vol).

17. The process according to claim 8, wherein said tail gas has a methane content of about 60% (vol) and a carbon monoxide content of about 2% (vol).

* * * * *